(12) United States Patent
Kato et al.

(10) Patent No.: US 8,423,301 B2
(45) Date of Patent: Apr. 16, 2013

(54) LIFETIME ASSESSMENT APPARATUS AND METHOD FOR OIL-FILLED ELECTRICAL DEVICE, AND DEGRADATION SUPPRESSION APPARATUS AND METHOD FOR OIL-FILLED ELECTRICAL DEVICE

(75) Inventors: Fukutaro Kato, Chiyoda-ku (JP); Eiichi Nagao, Chiyoda-ku (JP); Tsuyoshi Amimoto, Chiyoda-ku (JP); Satoru Toyama, Chiyoda-ku (JP); Kota Mizuno, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 337 days.

(21) Appl. No.: 12/831,500

(22) Filed: Jul. 7, 2010

(65) Prior Publication Data

US 2011/0202288 A1  Aug. 18, 2011

(30) Foreign Application Priority Data

Feb. 17, 2010 (JP) ................................ 2010-032081

(51) Int. Cl.
   *G01N 33/28* (2006.01)
   *G06F 19/00* (2011.01)
(52) U.S. Cl.
   USPC .............. 702/34; 702/23; 73/23.31; 73/25.05
(58) Field of Classification Search ...................... 702/34
   See application file for complete search history.

(56) References Cited

U.S. PATENT DOCUMENTS

| | | | |
|---|---|---|---|
| 5,309,776 A * | 5/1994 | Nanba et al. ..................... | 73/866 |
| 6,276,222 B1 | 8/2001 | Miyamoto et al. | |
| 2004/0107766 A1 * | 6/2004 | Bonne et al. .................. | 73/25.05 |
| 2005/0072964 A1 * | 4/2005 | Rapp et al. ..................... | 252/570 |
| 2009/0324808 A1 | 12/2009 | Gustafsson et al. | |

FOREIGN PATENT DOCUMENTS

| | | |
|---|---|---|
| CN | 101506917 A | 8/2009 |
| JP | 3516962 B2 | 4/2004 |
| JP | 2005259785 A * | 9/2005 |
| JP | 2010010439 A * | 1/2010 |
| WO | WO 98/56017 | 12/1998 |
| WO | WO 2010/073748 | 7/2010 |

OTHER PUBLICATIONS

Fukutaro Kato et al., Diagnostics for Copper Sulfide Deposition Using Highly Sensitive Analysis of Sulfur in Transformer Oil, the 29th Insulating Oil Committee Research Symposium, pp. 34-39, 2009.*

M. Dahlund et al., CIGRE WG A2-32, Copper sulphide in transformer insulation, Final Report Brochure 378, pp. 1-35, 2009.

(Continued)

*Primary Examiner* — Andrew Schechter
*Assistant Examiner* — Haidong Zhang
(74) *Attorney, Agent, or Firm* — Buchanan Ingersoll & Rooney PC

(57) ABSTRACT

An initial concentration of the residual concentration of a causative substance contained in an insulating oil is compared with a reference value. The causative substance reacts with a conductor forming a winding of an oil-filled electrical device to generate an electrically conductive compound. The reference value is defined as a value for determining whether a main determinant that determines the lifetime of the oil-filled electrical device is generation of the electrically conductive compound or degradation of insulating paper. Based on the initial concentration of the causative substance and the reference value, the lifetime of the oil-filled electrical device is assessed.

22 Claims, 12 Drawing Sheets

OTHER PUBLICATIONS

T. Amimoto et al., Duration and Mechanism for Suppressive Effect of Triazole-based Passivators on Copper-sulfide Deposition on Insulating Paper, IEEE Transactions on Dielectrics and Electrical Insulation, vol. 16, No. 1, pp. 257-264, 2009.

F. Scatiggio et al., "Corrosive Sulfur in Insulating Oils: Its Detection and Correlated Power Apparatus Failures," IEEE Transactions on Power Delivery, Jan. 2008, vol. 23, No. 1.

* cited by examiner

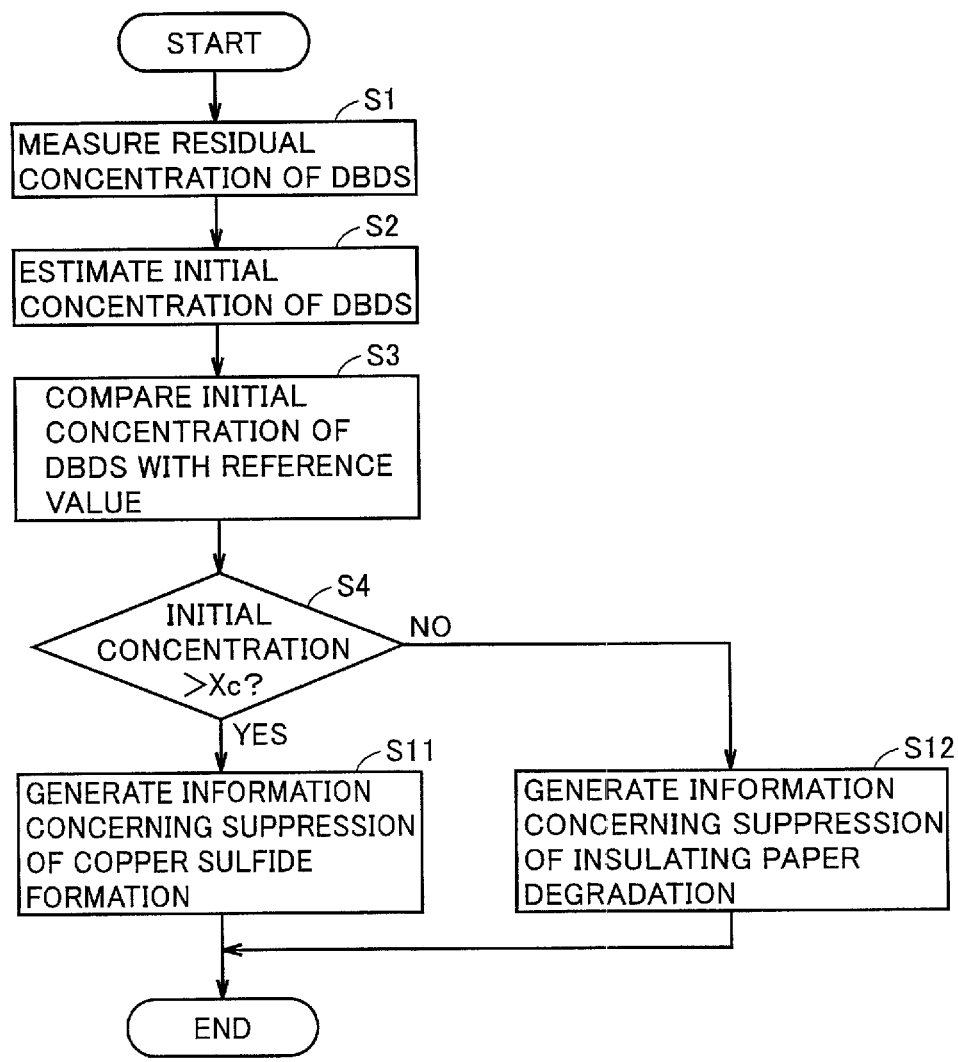

LIFETIME ASSESSMENT APPARATUS AND METHOD FOR OIL-FILLED ELECTRICAL DEVICE, AND DEGRADATION SUPPRESSION APPARATUS AND METHOD FOR OIL-FILLED ELECTRICAL DEVICE

BACKGROUND OF THE INVENTION

1. Field of the Invention

The present invention relates to an apparatus and a method for assessing the lifetime of an oil-filled electrical device, and to an apparatus and a method for suppressing degradation of an oil-filled electrical device.

2. Description of the Background Art

An oil-filled electrical device, particularly oil-filled transformer has a coil wire and insulating paper wrapped around the wire. The insulating paper provides electrical insulation between adjacent coil turns. While the transformer is used for a long period of time (several decades for example), the average degree of polymerization of cellulose molecules that form the insulating paper gradually decreases. Accordingly, the mechanical strength of the insulating paper gradually decreases.

In the case where short-circuit current flows in the transformer due to a system trouble, an electromagnetic force acts on the coil. The electromagnetic force is determined depending on the short-circuit current. When a large short-circuit current flows, a large electromagnetic force is generated on the coil and thus a tensile force is exerted on the coil insulating paper. When an excessive tensile force acts on the insulating paper which has been deteriorated, the insulating paper is broken. The breakage of the coil insulating paper causes deterioration of the electrical insulation property between adjacent coil turns. This is a typical mechanism that has a predominant influence on the lifetime of the transformer. It is therefore indispensable for assessment of the lifetime of the oil-filled electrical device to estimate the mechanical strength of the coil insulating paper.

As a method for preventing short circuit between coil turns due to decrease in mechanical strength of the insulating paper, an electrical device lifetime assessment method based on the degree of polymerization of the insulating paper has been proposed. The degree of polymerization of the insulating paper has a correlation with the mechanical strength of the insulating paper. The degree of polymerization of the insulating paper is therefore used for assessment of the lifetime of the electrical device (Patent Document 1: Japanese Patent No. 3516962 (WO98/056017)).

Patent Document 1 discloses a mathematical expression for calculating the degree of polymerization of insulating paper from the heating temperature and the heating years. According to Patent Document 1, the phenomenon of thermal degradation of insulating paper is different depending on whether the temperature is above or below 110° C. The above-referenced mathematical expression is derived from experiments in which an insulating oil having insulating paper therein is heated at a temperature of not more than 110° C. for a maximum of 12 years.

The relation between the mechanical strength of insulating paper and the degree of polymerization of the insulating paper is determined in advance. The degree of polymerization at the time when the mechanical strength of the insulating paper reaches a design limit value is the design limit value of the degree of polymerization of the insulating paper. The lifetime of the oil-filled electrical device can be assessed by estimating the degree of polymerization of the insulating paper.

A problem that a copper sulfide causes dielectric breakdown in an oil-filled electrical device has recently been reported. A sulfur component contained in an insulating oil reacts with a copper component in the insulating oil, so that an electrically conductive copper sulfide is deposited on insulating paper. The copper sulfide deteriorates the insulating property of the insulating paper. The deteriorated insulating property of the insulating paper results in dielectric breakdown (Non-Patent Document 1: CIGRE WG A2-32, "Copper sulphide in transformer insulation", Final Report Brochure 378, 2009).

Conventional lifetime assessment methods do not consider degradation of the insulating property due to deposition of the copper sulfide on the insulating paper, Therefore, the conventional methods may not correctly assess the lifetime of the oil-filled electrical device in some cases. In order to accurately analyze the state of the oil-filled electrical device, it is required to appropriately identify a main determinant that determines the lifetime of the oil-filled electrical device.

SUMMARY OF THE INVENTION

The present invention has been made to solve the above-described problem, and an object of the invention is to provide a technique for appropriately identifying a main determinant that determines the lifetime of an oil-filled electrical device.

According to an aspect of the present invention, a lifetime assessment apparatus for an oil-filled electrical device is a lifetime assessment apparatus for an oil-filled electrical device including a winding having a conductor covered with insulating paper, a tank containing the winding, and an insulating oil filling the tank. The lifetime assessment apparatus includes: a measurement unit configured to measure a residual concentration of a causative substance contained in the insulating oil and reacting with the conductor to generate an electrically conductive compound; a concentration estimate unit configured to estimate an initial concentration of the causative substance based on an operating time of the oil-filled electrical device and a measurement value of the residual concentration measured by the measurement unit; and a comparison unit configured to compare a reference value of the initial concentration with an estimate value of the initial concentration estimated by the concentration estimate unit. The reference value is defined as a value for determining whether a main determinant that determines a lifetime of the oil-filled electrical device is generation of the electrically conductive compound or degradation of the insulating paper. The lifetime assessment apparatus further includes an assessment unit configured to assess the lifetime of the oil-filled electrical device, based on a result of comparison between the estimate value and the reference value.

According to another aspect of the present invention, a degradation suppression apparatus for an oil-filled electrical device is a degradation suppression apparatus for an oil-filled electrical device including a winding having a conductor covered with insulating paper, a tank containing the winding, and an insulating oil filling the tank. The degradation suppression apparatus includes: a measurement unit configured to measure a residual concentration of a causative substance contained in the insulating oil and reacting with the conductor to generate an electrically conductive compound; a concentration estimate unit configured to estimate an initial concentration of the causative substance based on an operating time of the oil-filled electrical device and a measurement value of the residual concentration measured by the measurement unit; and a comparison unit configured to compare a reference value of the initial concentration with an estimate value of the initial concentration estimated by the concentration estimate unit. The reference value is defined as a value for determining whether a main determinant that determines a lifetime of the oil-filled electrical device is generation of the electrically conductive compound or degradation of the insulating paper. The degradation suppression apparatus further includes an information generation unit configured to generate information concerning a countermeasure for suppressing degradation of the oil-filled electrical device, based on a result of comparison between the estimate value and the reference value.

According to still another aspect of the present invention, a lifetime assessment method for an oil-filled electrical device is a lifetime assessment method for an oil-filled electrical device including a winding having a conductor covered with insulating paper, a tank containing the winding, and an insulating oil filling the tank. The lifetime assessment method includes the steps of: measuring a residual concentration of a causative substance contained in the insulating oil and reacting with the conductor to generate an electrically conductive compound; estimating an initial concentration of the causative substance based on an operating time of the oil-filled electrical device and a measurement value of the residual concentration; and comparing a reference value of the initial concentration with an estimate value of the initial concentration. The reference value is defined as a value for determining whether a main determinant that determines a lifetime of the oil-filled electrical device is generation of the electrically conductive compound or degradation of the insulating paper. The method further includes the step of assessing the lifetime of the oil-filled electrical device, based on a result of comparison between the estimate value and the reference value.

According to a further aspect of the present invention, a degradation suppression method for an oil-filled electrical device is a degradation suppression method for an oil-filled electrical device including a winding having a conductor covered with insulating paper, a tank containing the winding, and an insulating oil filling the tank. The degradation suppression method includes the steps of: measuring a residual concentration of a causative substance contained in the insulating oil and reacting with the conductor to generate an electrically conductive compound; estimating an initial concentration of the causative substance based on an operating time of the oil-filled electrical device and a measurement value of the residual concentration; and comparing a reference value of the initial concentration with an estimate value of the initial concentration. The reference value is defined as a value for determining whether a main determinant that determines a lifetime of the oil-filled electrical device is generation of the electrically conductive compound or degradation of the insulating paper. The method further includes the step of generating information concerning a countermeasure for suppressing degradation of the oil-filled electrical device, based on a result of comparison between the estimate value and the reference value.

In the manner as described above, the present invention can appropriately identify a main determinant that determines the lifetime of an oil-filled electrical device.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 15 is a flowchart for illustrating a degradation suppression method for an oil-filled electrical device in the second embodiment.

DESCRIPTION OF THE PREFERRED EMBODIMENTS

Figure 1:
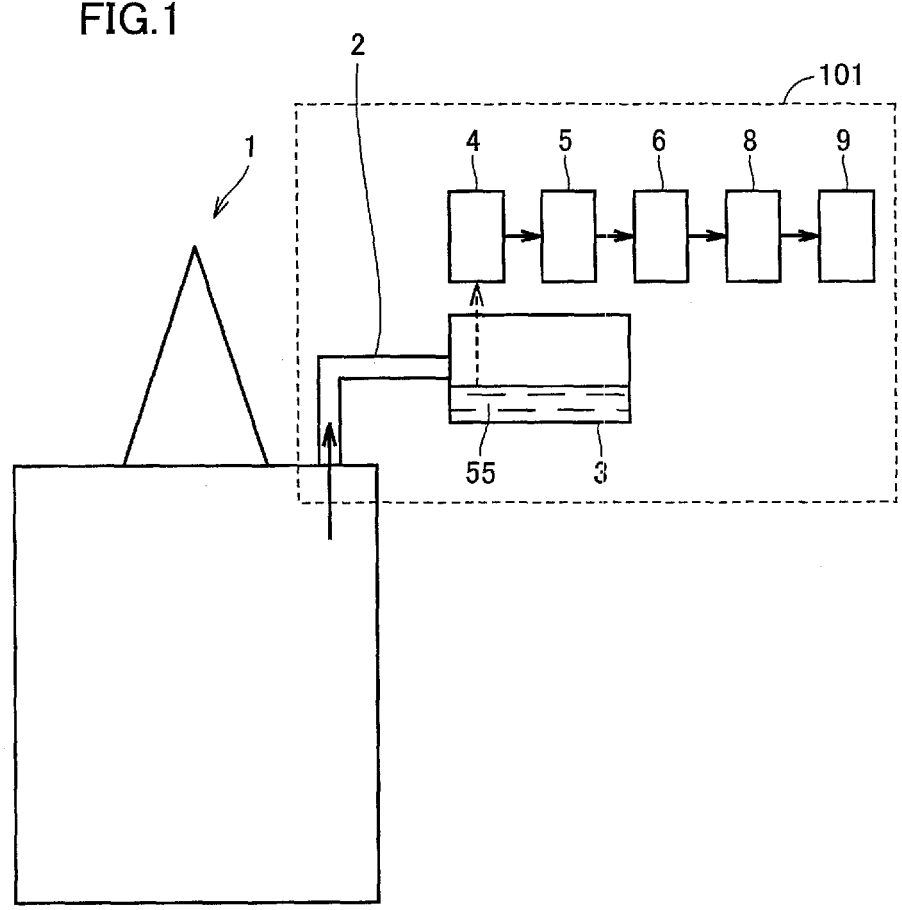
FIG. 1 is a configuration diagram of a lifetime assessment apparatus for an oil-filled electrical device in a first embodiment of the present invention.

Embodiments of the present invention will hereinafter be described in detail with reference to the drawings. In the drawings, the same or corresponding components are denoted by the same reference characters, and a description thereof will not be repeated.

First Embodiment

FIG. 1 is a configuration diagram of a lifetime assessment apparatus for an oil-filled electrical device in a first embodiment of the present invention. Referring to FIG. 1, assessment apparatus 101 includes a pipe 2, a tank 3, an oil pumping apparatus 4, a preprocessing apparatus 5, a concentration measuring instrument 6, a calculation unit 8, and a display 9.

Figure 2:
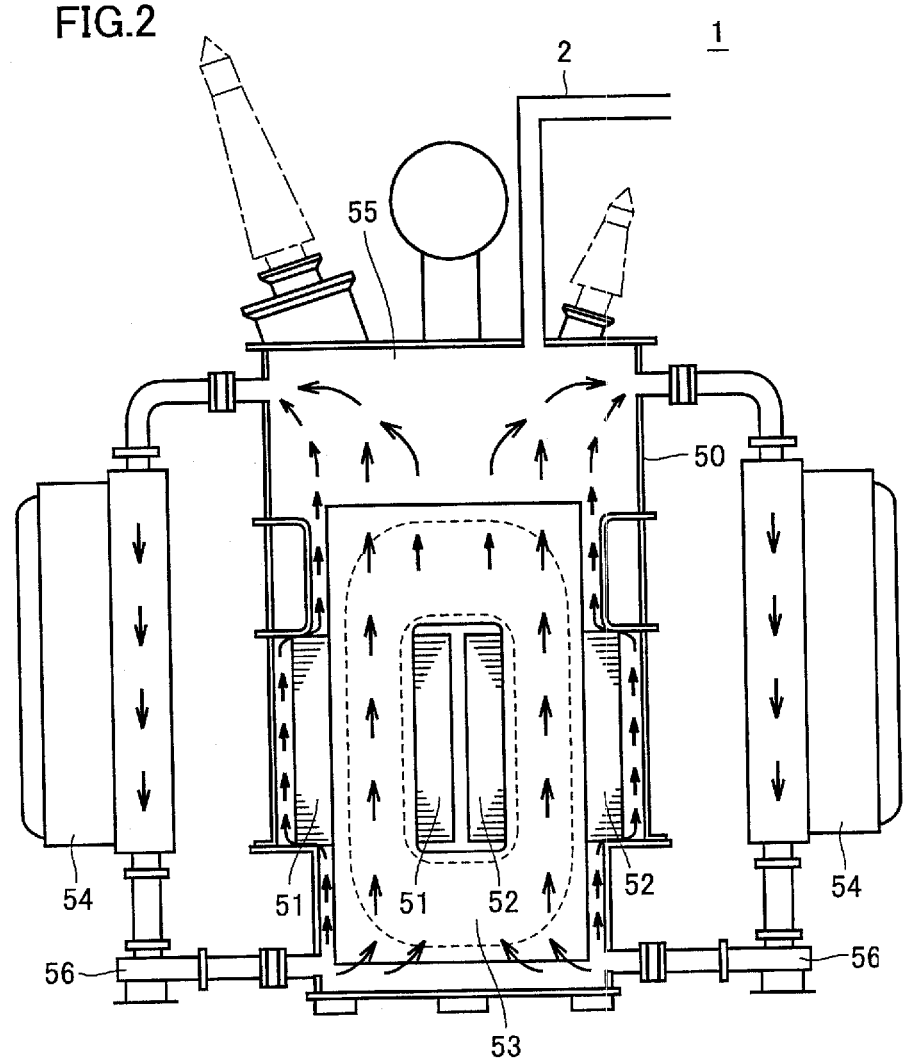
FIG. 2 is a cross section showing an example of a configuration of the oil-filled electrical device shown in FIG. 1.

FIG. 2 is a cross section showing an example of a configuration of the oil-filled electrical device shown in FIG. 1. Referring to FIG. 2, oil-filled electrical device 1 is a transformer for example, and includes a tank 50, cores 51, 52, a coil 53, a cooler 54, and an insulating oil 55.

Cores 51, 52 and coil 53 are housed in tank 50. Coil 53 is surrounded by cores 51, 52. The inside of tank 50 is filled with insulating oil 55. Coil 53 is therefore immersed in insulating oil 55.

Insulating oil 55 is circulated in oil-filled electrical device 1 by pump 56. As indicated by the arrows in FIG. 2, insulating oil 55 flows out of tank 50 to be cooled by cooler 54. Cooled insulating oil 55 then returns to tank 50. Insulating oil 55 is for example a mineral oil, synthetic oil or the like.

Figure 3:
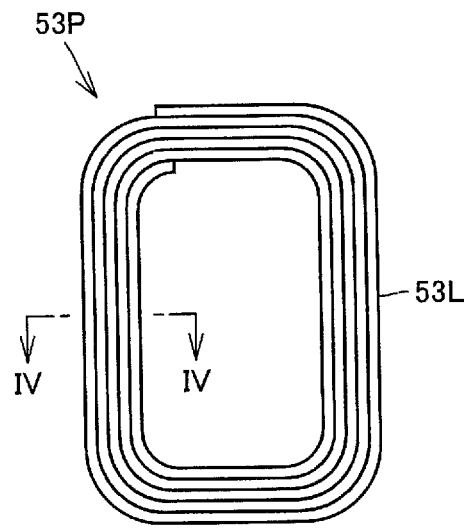
FIG. 3 is a plan view showing one of a plurality of winding layers forming a coil.
Figure 4:
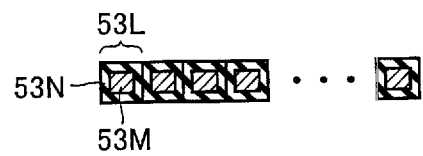
FIG. 4 is a cross section along line IV-IV of the winding layer shown in FIG. 3.

Coil 53 is constituted of a plurality of winding layers stacked along one direction. FIG. 3 is a plan view showing one of a plurality of winding layers that form the coil. FIG. 4 is a cross section along line IV-IV of the winding layer shown in FIG. 3.

Referring to FIGS. 3 and 4, a winding layer 53P is formed of a paper-wrapped conductor 53L. Paper-wrapped conductor 53L is coiled in the same plane. Paper-wrapped conductor 53L includes a conductor 53M containing copper and insulating paper 53N covering conductor 53M. Insulating paper 53N contains cellulose molecules.

Referring back to FIG. 1, tank 3 is connected by pipe 2 to oil-filled electrical device 1. When insulating oil 55 is to be taken from the inside of oil-filled electrical device 1, a part of the insulating oil in oil-filled electrical device 1 flows through pipe 2 to enter tank 3. Oil pumping apparatus 4 is for example a pump that takes the insulating oil in tank 3. The insulating oil in tank 3 is used for component analysis by means of concentration measuring instrument 6. Preprocessing apparatus 5 pre-processes the insulating oil in tank 3 before the insulating oil in tank 3 is delivered to concentration measuring instrument 6.

Concentration measuring instrument 6 measures the residual concentration of a causative substance of an electrically conductive compound. The causative substance of an electrically conductive compound refers to a substance that reacts with the conductor of the winding layer to generate the electrically conductive compound. Reaction of the causative substance with the conductor causes the concentration of the causative substance to gradually decrease. Thus, concentration measuring instrument 6 measures the residual concentration of the causative substance.

In the present embodiment, the causative substance with its concentration to be measured by concentration measuring instrument 6 is a sulfur compound, which is more specifically dibenzyl disulfide (di-benzyl-di-sulfide: DBDS). Concentration measuring instrument 6 is for example a gas chromatograph/mass spectrograph (GC/MS) for measuring the concentration of DBDS extracted from the insulating oil.

Calculation unit 8 is configured with a computer for example, and performs a calculation based on a map and a program stored in the calculation unit. Specifically, calculation unit 8 receives, from concentration measuring instrument 6, a measurement value of the residual concentration of DBDS. Based on the measurement value of the residual concentration of DBDS, the operating time of oil-filled electrical device 1, and the operating temperature of oil-filled electrical device 1, for example, calculation unit 8 assesses the lifetime of oil-filled electrical device 1. Specifically, calculation unit 8 estimates the remaining life of oil-filled electrical device 1, and outputs the estimate value.

Display 9 displays, on a screen (not shown), the result of assessment by calculation unit 8, namely the estimate value of the remaining life of oil-filled electrical device 1. In this way, the result of assessment by assessment apparatus 101 can be seen.

Figure 5:
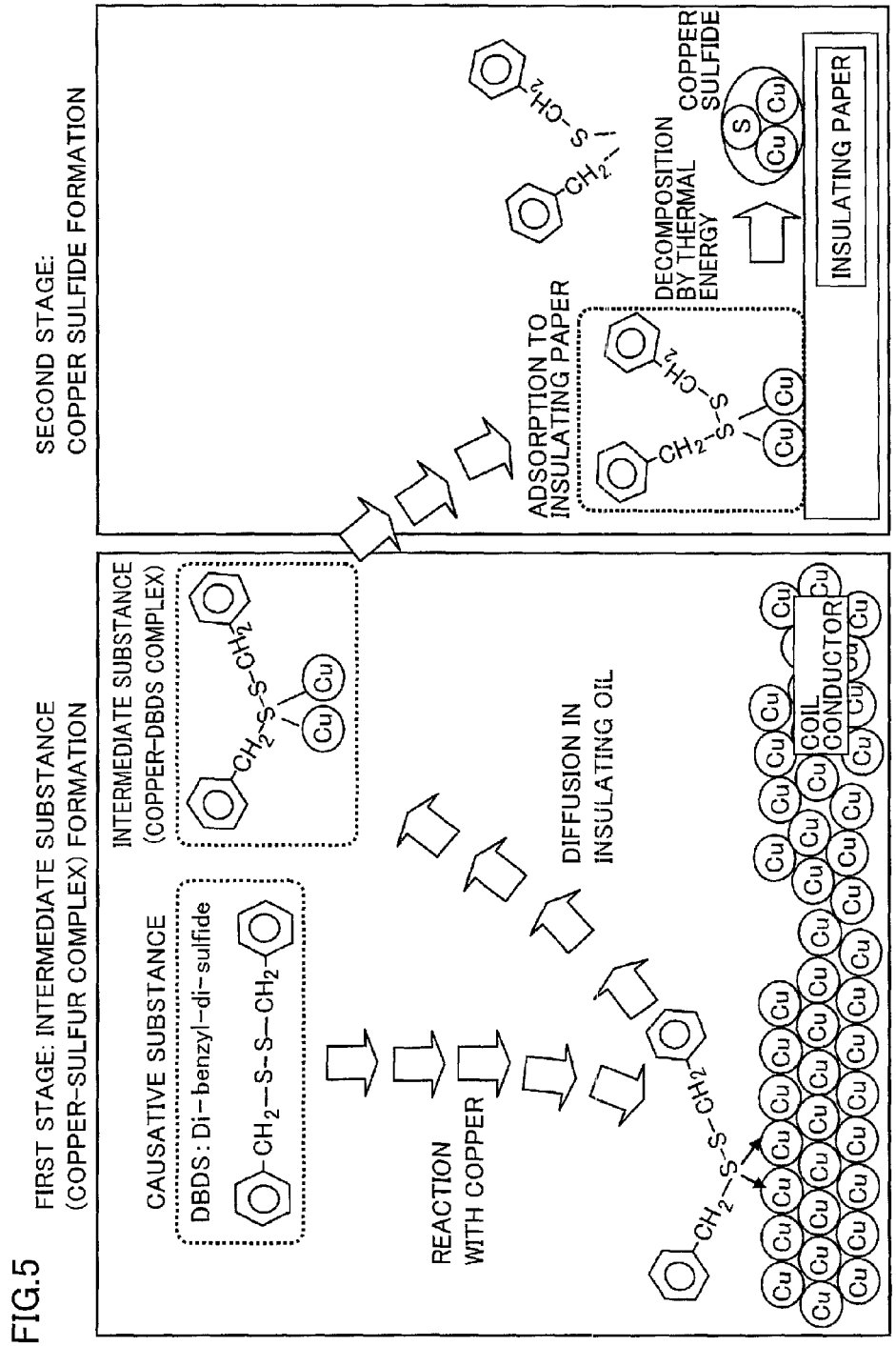
FIG. 5 is a schematic diagram for illustrating a mechanism of copper sulfide formation in an oil-filled electrical device.

FIG. 5 is a schematic diagram for illustrating a mechanism of copper sulfide formation in an oil-filled electrical device. Referring to FIG. 5, a copper sulfide formation reaction is constituted of two stages. In the first stage, copper and DBDS chemically react with each other to form a copper-DBDS complex. This complex diffuses in an insulating oil and a part of the complex adsorbs to insulating paper.

In the second stage, the above-described complex is decomposed by thermal energy, and a copper sulfide is deposited on the insulating paper. Because the copper sulfide is an electrically conductive substance, an electrically conductive path is formed with the origin located at the site where the copper sulfide is deposited. Consequently, coil turns adjacent to each other are short-circuited to cause dielectric breakdown.

The DBDS in the insulating oil is consumed through reaction of the DBDS with copper contained in the conductor of the coil. The DBDS concentration decreases with the operating years of the oil-filled electrical device. Therefore, in order to assess the risk of dielectric breakdown due to copper sulfide formation, it is necessary to estimate the initial concentration of DBDS. The initial concentration refers to the concentration at the time when the oil-filled electrical device starts being operated.

In the present embodiment, calculation unit 8 estimates, based on the residual concentration measured by concentration measuring instrument 6, the initial concentration of DBDS. Calculation unit 8 compares the estimate value of the initial concentration with a reference value of the DBDS concentration. The reference value is defined as a value for determining whether a main determinant that determines the lifetime of the oil-filled electrical device is the copper sulfide formation or insulating paper degradation. Calculation unit 8 assesses the lifetime of the oil-filled electrical device, based on the result of comparison between the reference value and the estimate value. The result of the assessment by calculation unit 8 reflects the main determinant as described above. In this way, the present embodiment can accurately assess the lifetime of the oil-filled electrical device.

Figure 6:
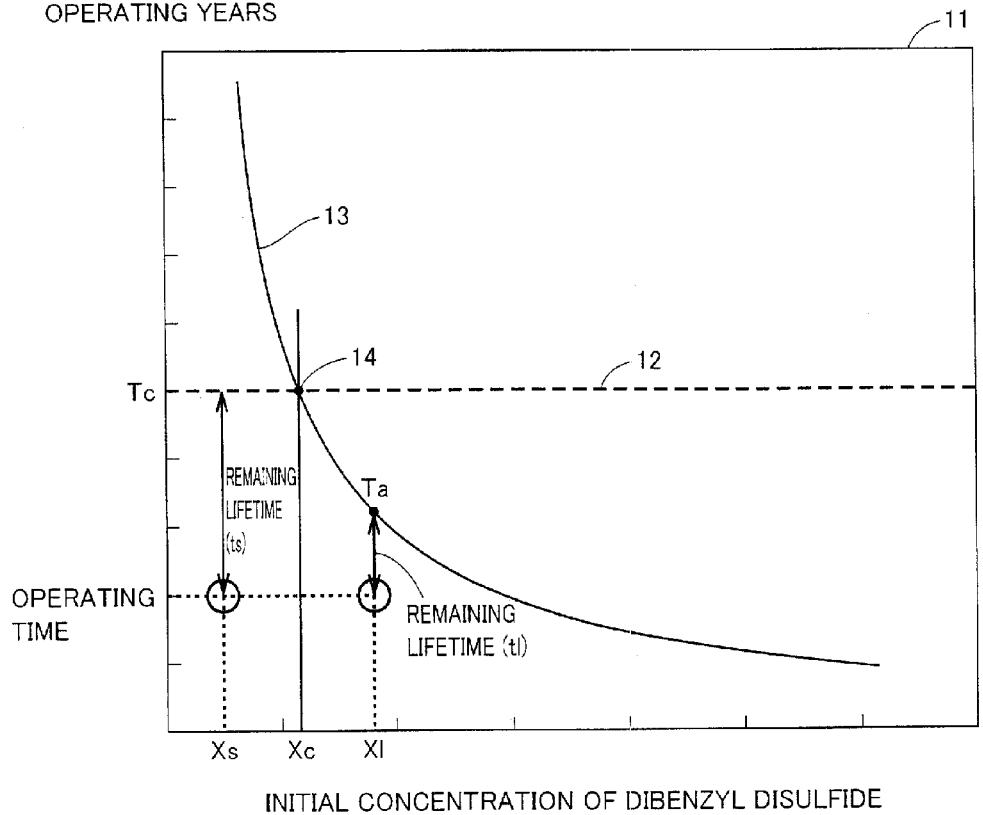
FIG. 6 is a diagram for illustrating lifetime assessment for an oil-filled electrical device based on a map.

Specifically, calculation unit 8 uses a map as described below to assess the lifetime of the oil-filled electrical device. FIG. 6 is a diagram for illustrating assessment of the lifetime of an oil-filled electrical device based on the map.

Referring to FIG. 6, map 11 defines a correlation between the initial concentration of DBDS at a predetermined operating temperature and the lifetime (in years) of an oil-filled electrical device. The horizontal axis of the graph represents the initial concentration of DBDS and the vertical axis of the graph represents the operating years.

Time Tc represents the operating period of time taken for the average degree of polymerization of insulating paper to reach a design limit value, at the aforementioned operating temperature. The mechanical strength of the insulating paper decreases with degradation of the insulating paper. The average degree of polymerization of the insulating paper (cellulose molecules) has a correlation with the mechanical strength of the insulating paper. The design limit value of the average degree of polymerization of the insulating paper corresponds to the value at the time when the mechanical strength of the insulating paper reaches a design limit value of the mechanical strength.

The average degree of polymerization of the insulating paper does not depend on the initial concentration of DBDS but depends on only the temperature of the insulating oil and the operating years of the oil-filled electrical device. Time Tc can therefore be determined in advance using for example the mathematical expression disclosed in Patent Document 1. The relation between the operating time taken for the average degree of polymerization of the insulating paper to reach the design limit value, and the initial concentration of DBDS, is represented on the graph by the straight line (broken line 12) running in parallel with the horizontal axis.

In contrast, the rate of copper sulfide formation depends on the initial concentration of the causative substance (DBDS). A curve 13 represents a relation between the initial concentration of DBDS and the time taken for generation of a copper sulfide of an amount that causes dielectric breakdown of the insulating paper. A higher initial concentration of DBDS results in a shorter time taken for generation of a copper sulfide of the amount that causes dielectric breakdown of the insulating paper. Namely, as the initial concentration of DBDS is higher, the lifetime of oil-filled electrical device 1 is shorter.

Xc represents the initial concentration of DBDS that corresponds to the point of intersection of broken line 12 and curve 13, and corresponds to "reference value" as described above. In other words, Xc represents the initial concentration of DBDS in the case where the operating time taken for dielectric breakdown to occur due to deposition of a copper sulfide is equal to the operating time taken for the average degree of polymerization of the insulating paper to reach the design limit value.

In the present embodiment, different lifetime assessment methods are used depending on whether the initial concentration of DBDS is larger than Xc. When the initial concentration is Xs which is a value smaller than Xc, the time taken for the average degree of polymerization of the insulating paper to reach the design limit value is shorter than the time taken for a copper sulfide of an amount to be formed that causes dielectric breakdown of the insulating paper. Therefore, in the case where the initial concentration is smaller than the reference value, decrease in average degree of polymerization of the insulating paper is a main determinant that determines the lifetime of the oil-filled electrical device. Then, calculation unit 8 estimates the remaining lifetime of the oil-filled electrical device by calculating a difference is between time Tc and the operating time of the oil-filled electrical device.

In contrast, when the initial concentration is Xl which is a value larger than Xc, the time (Ta) taken for a copper sulfide of an amount that causes dielectric breakdown of the insulating paper to be formed is shorter than the time (Tc) for the average degree of polymerization of the insulating paper to reach the design limit value. Therefore, when the initial concentration is larger than the reference value, the copper sulfide formation is a main determinant that determines the lifetime of the oil-filled electrical device. In this case, the lifetime of the oil-filled electrical device depends on the rate at which the copper sulfide is formed, and therefore, the conventional lifetime assessment method, namely the lifetime assessment method based on the average degree of polymerization of the insulating paper, cannot accurately assess the lifetime of the device. Then, calculation unit 8 estimates that the remaining lifetime of the oil-filled electrical device is equal to difference t1 between time Ta and the operating time.

As shown in FIG. 6, map 11 defines the lifetime of the oil-filled electrical device so that the lifetime of the oil-filled electrical device depends on one of the average degree of polymerization of the insulating paper and the initial concentration of DBDS. Specifically, a parameter that has a predominant influence on the lifetime is determined based on which of the initial concentration of DBDS and the reference value (Xc) is larger/smaller. When the initial concentration of DBDS is smaller than the reference value, the average degree of polymerization of the insulating paper has a predominant influence on the lifetime. In contrast, when the initial concentration of DBDS is larger than the reference value, the initial concentration of DBDS has a predominant influence on the lifetime. Namely, the shorter one of the operating time taken for the average degree of polymerization of the insulating paper to become equal to or lower than the design limit value and the operating time taken for a copper sulfide to be formed to cause dielectric breakdown is defined as the lifetime of the oil-filled electrical device.

For a different operating temperature, the time taken for the average degree of polymerization of the insulating paper to reach the design limit value and the lifetime that depends on the rate of copper sulfide formation may be different. Therefore, a map similar to map 11 shown in FIG. 6 may be prepared for a certain operating temperature.

Figure 7:
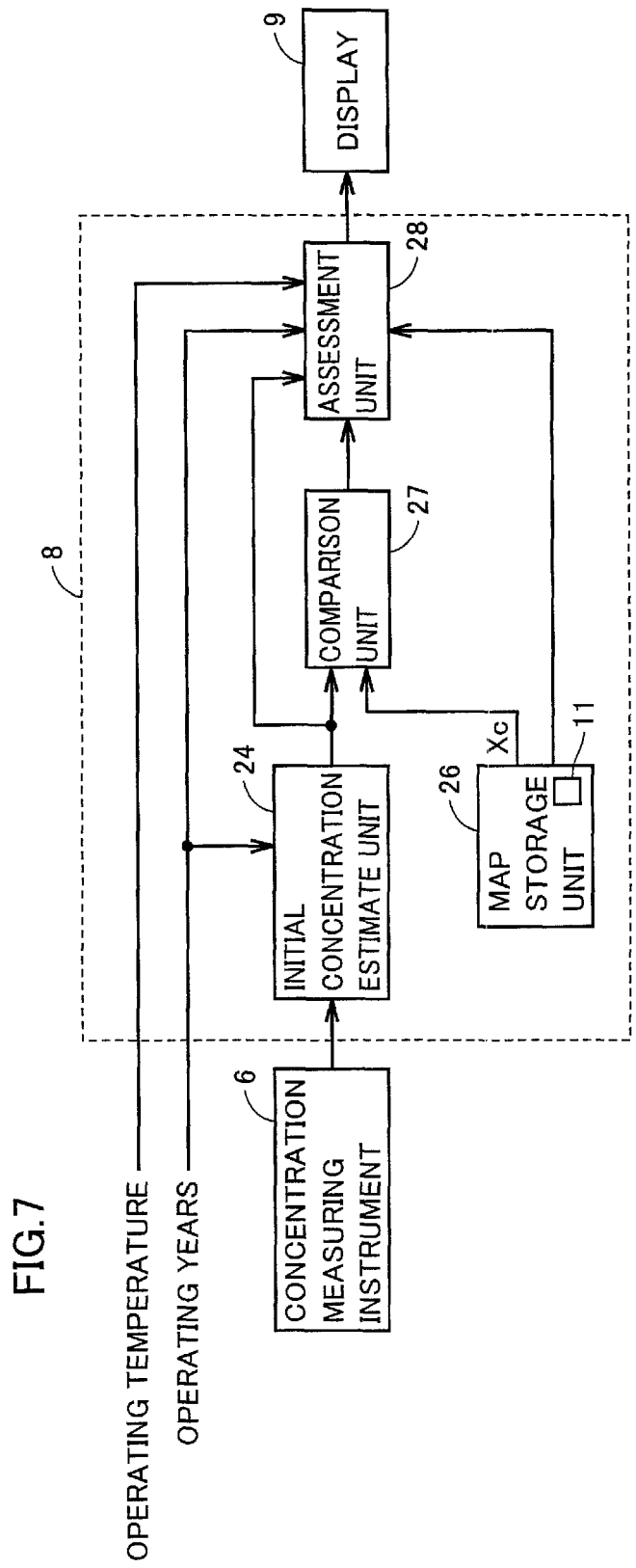
FIG. 7 is a functional block diagram showing a configuration of a calculation unit shown in FIG. 1.

A description will now be given of a configuration of the calculation unit for assessing the lifetime of an oil-filled electrical device following the map shown in FIG. 6. FIG. 7 is a functional block diagram showing the configuration of the calculation unit shown in FIG. 1.

Referring to FIG. 7, calculation unit 8 includes an initial concentration estimate unit 24, a map storage unit 26, a comparison unit 27, and an assessment unit 28.

Initial concentration estimate unit 24 estimates the initial concentration of DBDS based on the residual concentration of DBDS measured by concentration measuring instrument 6, and outputs the estimate value to assessment unit 28. Map storage unit 26 stores map 11 (see FIG. 6). In the case where a plurality of maps are prepared respectively for different operating temperatures of the oil-filled electrical device (different temperatures of the insulating oil for example), map storage unit 26 stores the plurality of maps.

Comparison unit 27 receives the estimate value of the initial concentration of DBDS from initial concentration estimate unit 24, and also receives reference value Xc of the initial concentration of DBDS from map storage unit 26. Comparison unit 27 makes a comparison between the estimate value and the reference value and outputs the result of the comparison.

Following the method described above, assessment unit 28 assesses the lifetime of oil-filled electrical device 1. Specifically, based on the result of comparison by comparison unit 27, the estimate value of the initial concentration of DBDS, the operating time and the operating temperature of the oil-filled electrical device, and map 11 stored in map storage unit 26, assessment unit 28 assesses the lifetime of oil-filled electrical device 1. When the fact that the initial concentration of DBDS is higher than the reference value is derived from the result of the comparison by comparison unit 27, assessment unit 28 subtracts the operating time from the lifetime (time Ta in FIG. 6) determined based on the initial concentration of DBDS to calculate the remaining lifetime of the oil-filled electrical device. In contrast, the fact that the initial concentration of DBDS is lower than the reference value is derived from the result of the comparison by comparison unit 27, assessment unit 28 subtracts the operating time from the lifetime (time Tc in FIG. 6) determined based on the average degree of polymerization of the insulating paper to calculate the remaining lifetime of the oil-filled electrical device.

Assessment unit 28 outputs the calculated remaining life to display 9. Display 9 then displays the remaining life.

Figure 8:
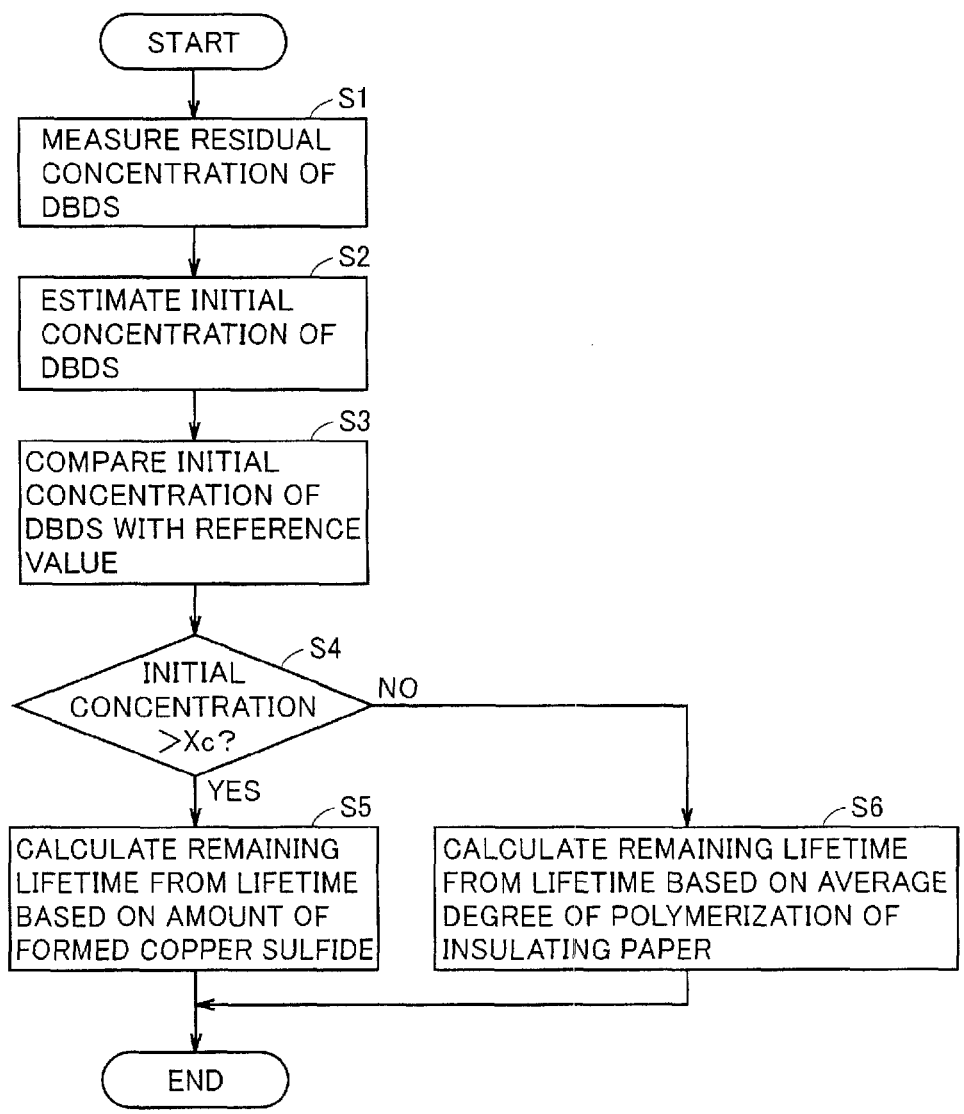
FIG. 8 is a flowchart for illustrating a lifetime assessment method for an oil-filled electrical device in the first embodiment.

FIG. 8 is a flowchart for illustrating a lifetime assessment method for an oil-filled electrical device in the first embodiment. The process of this flowchart is executed when, for example, the oil-filled electrical device is inspected.

Referring to FIG. 8, in step S1, concentration measuring instrument 6 measures the residual concentration of DBDS by component analysis of the insulating oil in tank 3. In step S2, calculation unit 8 estimates the initial concentration of DBDS based on the residual concentration of DBDS. A method for estimating the initial concentration will be described later in detail.

In step S3, calculation unit 8 compares the initial concentration with reference value Xc. In step S4, it is determined whether the initial concentration of DBDS is larger than reference value Xc. When it is determined that the initial concentration is larger than Xc (YES in step S4), the process proceeds to step S5. When it is determined that the initial concentration is smaller than Xc (NO in step S4), the process proceeds to step S6.

In step S5, calculation unit 8 calculates the remaining life from the lifetime determined based on the rate of formation of a copper sulfide (corresponding to Ta in FIG. 6) and the operating time of oil-filled electrical device 1. In step S6, calculation unit 8 calculates the remaining life from the lifetime determined based on the average degree of polymerization of the insulating paper (corresponding to Tc in FIG. 6) and the operating time of the oil-filled electrical device. The operations in steps S5 and S6 are performed for assessing the lifetime of oil-filled electrical device 1. When the operation of step S5 or S6 is completed, the whole process is accordingly completed.

In accordance with the present embodiment, the lifetime of a transformer can be assessed based on the estimated remaining life. A measure such as update (replacement) of the transformer can thus be proposed.

Method for Estimating Initial Concentration of DBDS

The initial concentration of DBDS can be estimated by adding a decrease in DBDS concentration to the residual concentration of DBDS. A method for estimating the decrease in DBDS in the insulating oil may be selected from various methods. For example, from the relation between the equivalent temperature and the amount of formed copper sulfide, the amount of formed copper sulfide may be estimated (Non-Patent Document 2: Fukutaro Kato, Tsuyoshi Amimoto, Nagao Eiichi, Noboru Hosokawa, Satoru Toyama, Junji Tanimura, "Diagnostics for Copper Sulfide Deposition Using Highly Sensitive Analysis of Sulfur in Transformer Oil", the 29th Insulating Oil Committee Research Symposium, pp. 34-39, 2009).

In the present embodiment, a decrease in DBDS concentration is calculated by determining the product of the average rate of decrease and the operating time. "Average rate of decrease" used in the present embodiment is the rate of decrease in DBDS concentration at the equivalent temperature of a coil. The average rate of decrease is determined in advance, for example, through Processes 1 to 3 as follows:

Process 1: a process of obtaining the relation between the operational load factor and the environmental temperature of a transformer, and the coil temperature in the transformer, from test data of the transformer;

Process 2: a process of calculating the equivalent temperature of the coil in the transformer from the information about the operational load factor and the environmental temperature of the transformer as well as the relation obtained in Process 1; and Process 3: a process of calculating the average rate of decrease at the equivalent temperature of the coil.

In Process 1, a heat run test is conducted for example for the transformer. The heat run test is conducted for measuring a temperature increase under a predetermined load condition for obtaining characteristics of cooling windings and iron cores. By way of example, a heat run test is performed, following the equivalent loading method using short circuit, based on JEC (Japanese Electrotechnical Committee)-2200. This test measures the oil temperature at a bottom portion and an upper portion of the transformer. The temperature of the coil winding is calculated from the resistance value of the coil as measured.

Figure 9:
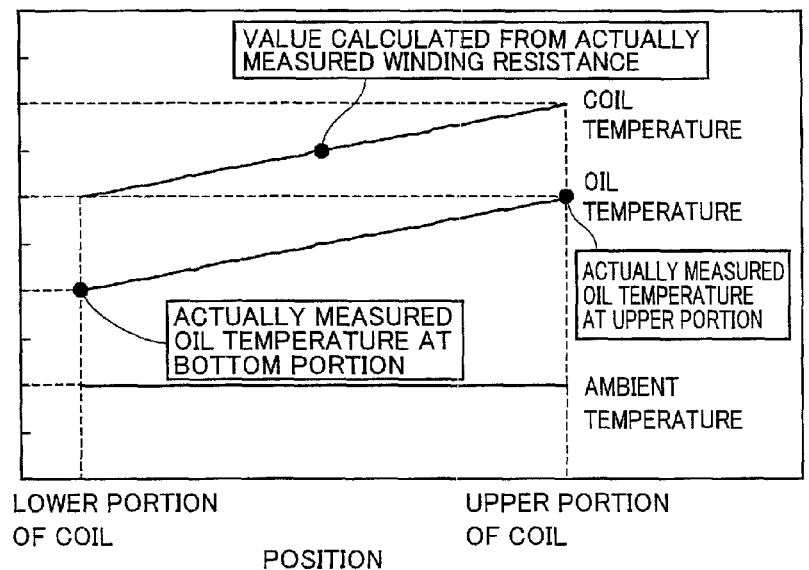
FIG. 9 is a diagram schematically showing the temperature of an insulating oil and the temperature of a coil winding in a transformer that are determined by a heat run test.

FIG. 9 is a diagram schematically showing the temperature of an insulating oil and the temperature of a coil winding in a transformer that are determined by a heat run test. Referring to FIG. 9, heat is generated from the coil winding due to applied current. As a result, the oil temperature is lowest at a lower portion of the coil and is highest at an upper portion of the coil.

Figure 10:
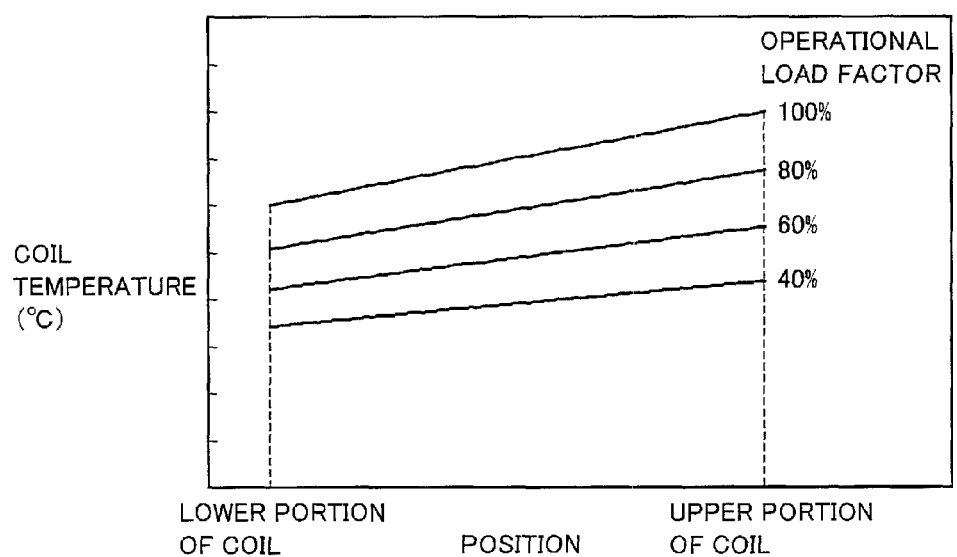
FIG. 10 is a diagram schematically showing a relation between an operational load factor and a coil temperature.

Based on this method, the temperature of the insulating oil at a bottom portion of the transformer and that at an upper portion of the transformer, in the case where the transformer is operated at a certain operational load factor under a certain environmental temperature condition, are measured. As shown in FIG. 10, from the measured temperature of the insulating oil, the coil temperature at each portion of the transformer (bottom portion and upper portion for example) using operational load factors as parameters is obtained. FIG. 10 schematically shows a relation between the operational load factor and the coil temperature. The operational load factor is, for example, 40%, 60%, 80%, and 100%, The operational load factor is not limited to these values.

Figure 11:
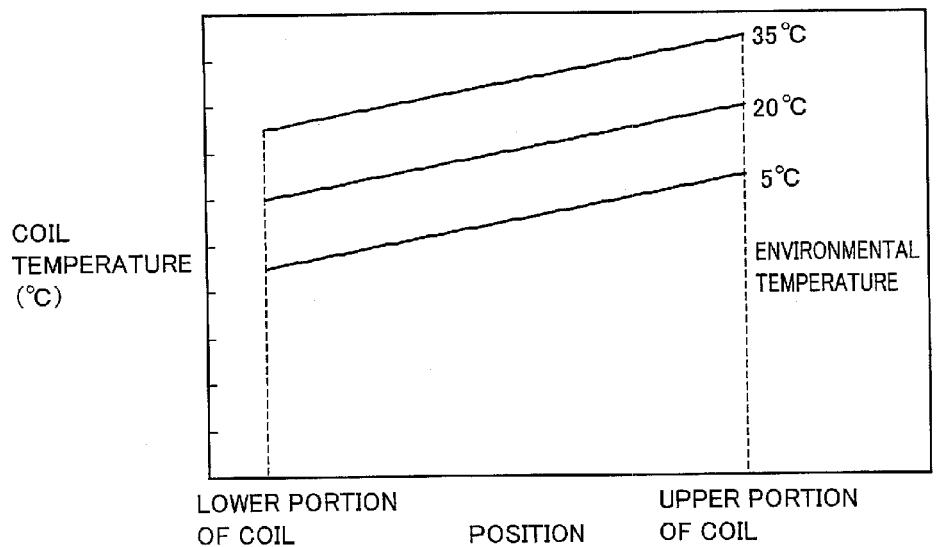
FIG. 11 is a diagram schematically showing a relation between an environmental temperature and a coil temperature.

Further, the temperature of the insulating oil at the bottom portion and that at the upper portion of the transformer, in the case where the transformer is operated at a certain operational load factor under a certain environmental temperature condition, are measured. As shown in FIG. 11, from the measured temperature of the insulating oil, the coil temperature at each portion of the transformer (bottom portion and upper portion for example), in the case where the environmental temperature is used as a parameter, is obtained. FIG. 11 schematically shows the relation between the environmental temperature and the coil temperature. The environmental temperature is 5° C., 20° C., and 35° C. for example. The environmental temperature is not limited to these values.

Following the method as described above, the relation between the operational load factor and the environmental temperature of the transformer, and the coil temperature in the transformer, is obtained.

In Process 2, the average environmental temperature is determined first. The temperature in an environment in which the transformer is installed is not constant. Consideration can be given to variation in temperature in a day and over a year to determine the average environmental temperature over the whole operating period for the transformer.

Next, the average operational load factor of the oil-filled electrical device is determined. The average operational load factor is an average value of the operational load factor in the operating period of the transformer. The average operational load factor is calculated, for example, based on data recorded at the installation site of the transformer (substation for example).

Subsequently, the equivalent temperature of the coil is determined. The relation obtained in Process 1, namely the relation between the operational load factor and the environmental temperature of the transformer, and the coil temperature in the transformer, is used. This relation can be used to determine the coil temperature at each portion (bottom portion and upper portion for example) in the transformer at the average environmental temperature and the average operational load factor.

Then, the relation between the coil temperature and the rate of decrease in DBDS concentration at each portion in the transformer is obtained. Generally, a lower portion of the coil has the lowest coil temperature and an upper portion of the coil has the highest coil temperature. The reaction between DBDS and copper has temperature dependency. Specifically, a higher temperature provides a higher reaction rate and a higher rate of decrease in DBDS concentration. At the lower portion of the coil having a lower temperature, the rate of decrease in DBDS concentration is smaller. In contrast, at the upper portion of the coil having a higher temperature, the rate of decrease in DBDS concentration is higher.

In the case of a chemical reaction in which a copper sulfide is formed, the rate of reaction is doubled with respect to an increase of the temperature by 10° C. for example. Based on this temperature dependency, it is presumed that the rate of decrease in DBDS concentration is doubled with respect to an increase in coil temperature by 10° C. Based on this presumption, a graph illustrating a relation between the coil temperature at each portion (bottom portion and upper portion for example) in the transformer and the rate of decrease in DBDS concentration is prepared.

Figure 12:
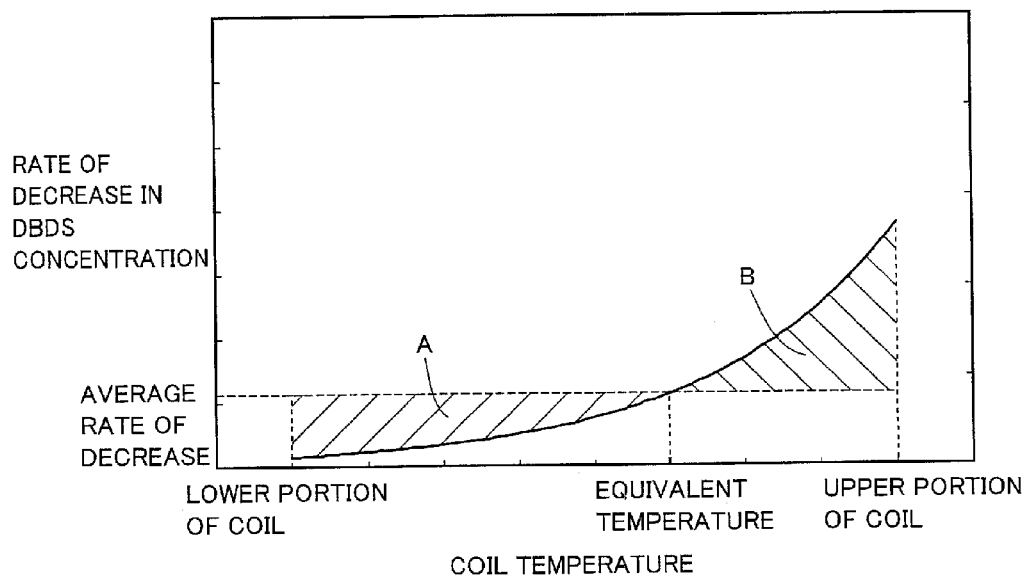
FIG. 12 is a diagram schematically showing a relation between a coil temperature and a rate of decrease in DBDS concentration.

FIG. 12 is a diagram schematically illustrating a relation between the coil temperature and the rate of decrease in DBDS concentration. Referring to FIG. 12, the temperature at which the value representing the area of region A and the value representing the area of region B are equal to each other is determined as the equivalent temperature of the coil.

In Process 3, based on the relation shown in FIG. 12, the rate of decrease in DBDS concentration at the equivalent temperature is obtained. Calculation unit 8 (initial concentration estimate unit 24) stores the rate of decrease in advance, so that calculation unit 8 can estimate an amount of decrease in DBDS concentration.

As heretofore described, the first embodiment compares the initial concentration of DBDS with a reference value. The reference value is defined as a value for determining whether a main determinant that determines the lifetime of the oil-filled electrical device is copper sulfide formation or degradation of insulating paper. The first embodiment therefore can appropriately identify the main determinant that determines the lifetime of the oil-filled electrical device.

Further, the first embodiment combines the method for assessing the lifetime of the oil-filled electrical device based on the average degree of polymerization of the insulating paper, and the method for assessing the lifetime of the oil-filled electrical device based on the initial concentration of DBDS. The estimate value of the initial concentration of DBDS is compared with a reference value to select one of the two methods. The first embodiment can appropriately identify the main determinant that determines the lifetime of the oil-filled electrical device and therefore, accurately assess the lifetime of the oil-filled electrical device.

Second Embodiment

In a second embodiment, information about a countermeasure for suppressing degradation of an oil-filled electrical device can be obtained.

Figure 13:
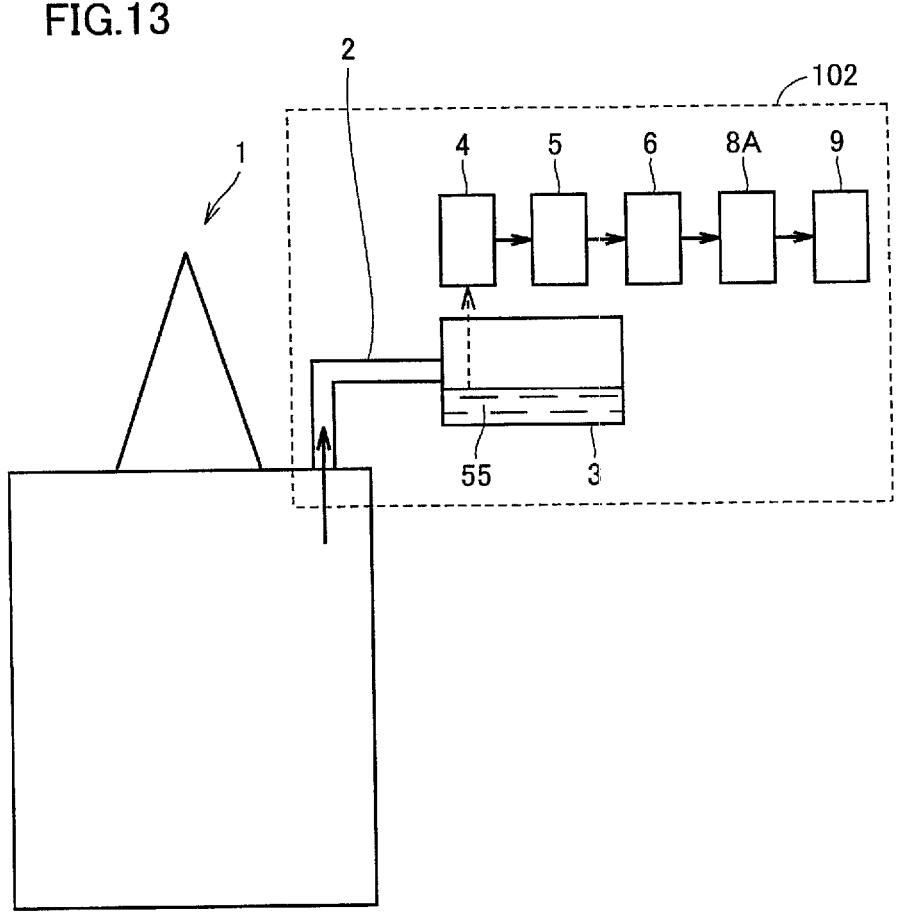
FIG. 13 is a configuration diagram of a degradation suppression apparatus for an oil-filled electrical device in a second embodiment of the present invention.

FIG. 13 is a configuration diagram of a degradation suppression apparatus for an oil-filled electrical device in the second embodiment of the present invention. Referring to FIGS. 13 and 1, degradation suppression apparatus 102 differs from assessment apparatus 101 in that a calculation unit 8A replaces calculation unit 8. The features of other components of degradation suppression apparatus 102 are similar to those of corresponding components of assessment apparatus 101, and the detailed description thereof will not be repeated.

Calculation unit 8A estimates the initial concentration of DBDS based on the residual concentration of DBDS measured by concentration measuring instrument 6. Further, calculation unit 8A compares the estimate value with a reference value. "Reference value" is a value used for determining whether a main determinant that determines the lifetime of the oil-filled electrical device is copper sulfide formation or degradation of insulating paper. Specifically, Xc shown in FIG. 6 is used as the reference value. Based on the result of the comparison between the estimate value and the reference value, calculation unit SA generates information concerning a countermeasure for suppressing degradation of oil-filled electrical device 1, and outputs the information. Display 9 displays the information that is output from calculation unit 8A, on a screen (not shown). Based on the information displayed on display 9, the countermeasure for suppressing degradation of oil-filled electrical device 1 can be implemented. The countermeasure for suppressing degradation of oil-filled electrical device 1 is different depending on which of the initial concentration of DBDS and reference value Xc is larger/smaller.

When the initial concentration of DBDS is smaller than Xc (Xs<Xc as shown in FIG. 6), a countermeasure for suppressing decrease of the average degree of polymerization of the insulating paper is selected. It is an effective countermeasure for suppressing decrease of the average degree of polymerization of the insulating paper to lower the operating temperature. Examples of the method for lowering the temperature may include reduction of the operational load of the oil-filled electrical device, reinforcement of the cooling ability by adding cooling fans, and change of the method for operating the cooling fan. An example of the method for reducing the operational load of the oil-filled electrical device may be adjustment of the share of the operational load of the oil-filled electrical device incorporated in an electric power system. This method, for example, reduces the applied current flowing in a degraded device while increasing the applied current flowing in other normal devices. In this way, the operational load on the deteriorated device can be lessened.

In contrast, when the initial concentration of DBDS is larger than Xc (Xl>Xc shown in FIG. 6), a countermeasure for suppressing copper sulfide formation is selected. It is effective, as a countermeasure for suppressing copper sulfide formation, to replace the oil in use with an oil without containing DBDS which is a causative substance, to process the oil in use (remove a sulfur component for example), and to add a suppressing agent to the insulating oil for suppressing copper sulfide formation.

As the suppressing agent, for example, 1,2,3-benzotriazole (BTA) and/or N,N-bis(2-ethylhexyl)-(4 or 5)-methyl-1H-benzotriazole-1-methylamine may be applied (for example, Non-Patent Document 3: T. Amimoto, E. Nagao, J. Tanimura, S. Toyama, and N. Yamada "Duration and Mechanism for Suppressive Effect of Triazole-based Passivators on Copper-Sulfide Deposition on Insulating Paper", IEEE Transactions on Dielectrics and Electrical Insulation, Vol. 16, No. 1, pp. 257-264, 2009). The above-referenced additive is added to adhere to the surface of copper and form a complex coating. The coating interferes with the chemical reaction between a sulfur component and copper in the insulating oil and thereby suppresses formation of a copper sulfide.

Further, a chelating agent that inactivates a copper-DBDS complex may be added to the insulating oil. The deactivation of the copper-DBDS complex suppresses deposition of copper sulfide on the insulating paper. The chelating agent is selected, for example, from the following substances: ethylenediamine, piperidine, ethylenediaminetetraacetic acid, phenanthroline, porphyrin, crownetherr, acetylacetone, aminotriazole, alizarin, oxine, morin, quinaldine acid, aluminon, and triethanolamine. Preferably, the chelating agent is selected from the group consisting of ethylenediamine, ethylendiaminetetraacetic acid, and acetylacetone.

Figure 14:
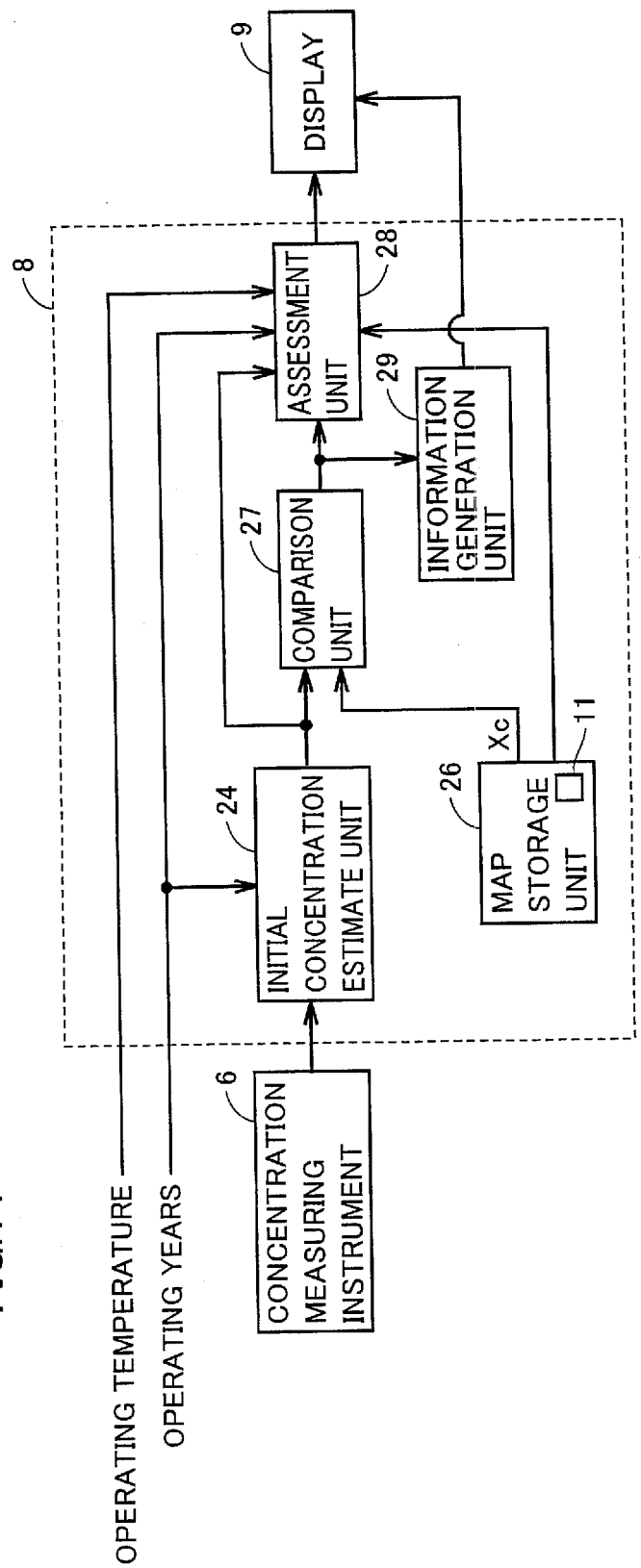
FIG. 14 is a functional block diagram showing a configuration of a calculation unit shown in FIG. 13.

FIG. 14 is a functional block diagram showing a configuration of the calculation unit shown in FIG. 13. Referring to FIGS. 13 and 7, calculation unit 8A differs from calculation unit 8 in that the former further includes an information generation unit 29. Features of other components are similar to those of corresponding components of calculation unit 8. Here, assessment unit 28 may not be included.

Information generation unit 29 receives the result of comparison by comparison unit 27. Comparison unit 27 compares the estimate value of the initial concentration of DBDS with a reference value.

When the fact that the estimate value is smaller than the reference value is indicated by the result of comparison, information generation unit 29 generates information for suppressing degradation of the insulating paper. The information is, for example, information showing that it is necessary to decrease the operating temperature. Display 9 presents on a screen (not shown) the information for suppressing degradation of the insulating paper, for example, information representing a decrease in operating temperature.

In contrast, when the fact that the estimate value is larger than the reference value is indicated by the result of comparison, information generation unit 29 generates information for suppressing copper sulfide formation. This information is information showing replacement of the insulating oil, for example. Display 9 presents on a screen (not shown) information for suppressing copper sulfide formation, for example, information representing replacement of the insulating oil.

FIG. 15 is a flowchart for illustrating a method for suppressing degradation of an oil-filled electrical device in the second embodiment. The process of this flowchart is executed, for example, when a routine inspection is conducted for the oil-filled electrical device.

Referring to FIGS. 15 and 8, the method for suppressing degradation of an oil-filled electrical device is different from the lifetime assessment method for an oil-filled electrical device in that operations in steps S11 and S12 are included instead of the operations in steps S5 and S6. Respective operations performed in steps S1 to S4 shown in FIG. 15 are similar to the operations in the corresponding steps in the flowchart of FIG. 8. In step S4, it is determined whether the initial concentration of DBDS is larger than reference value Xc. When it is determined that the initial concentration is larger than Xc (YES in step S4), the process proceeds to step S11. In contrast, when it is determined that the initial concentration is smaller than Xc (NO in step S4), the process proceeds to step S12.

In step S11, calculation unit 8A generates information concerning suppression of copper sulfide formation. In step S12, calculation unit 8A calculates the remaining life from the lifetime determined based on the average degree of polymerization of the insulating paper (corresponding to Tc in FIG. 6) and the operating time of the oil-filled electrical device. When the operation in step S11 or S12 is completed, the whole process has come to the end.

Preferably, a countermeasure for suppressing degradation is implemented as early as possible. Because the oil-filled electrical device has been installed in the electric power system, electrical power failure occurs if the device is immediately stopped. Therefore, a countermeasure for suppressing degradation is preferably implemented at the time when a routine inspection is conducted for which the device is stopped.

In the second embodiment, like the first embodiment, the initial concentration of DBDS is compared with a reference value. The second embodiment thus can appropriately identify a main determinant that determines the lifetime of the oil-filled electrical device.

Further, in the second embodiment, the main determinant that determines the lifetime of the oil-filled electrical device can be appropriately identified, and therefore, information concerning an appropriate countermeasure for suppressing degradation of the oil-filled electrical device can be generated. Then, the countermeasure following the information can be implemented to effectively suppress degradation of the oil-filled electrical device. The degradation of the oil-filled electrical device is thus suppressed so that the lifetime of the oil-filled electrical device can be extended.

According to the above-described first and second embodiments, the average degree of polymerization of insulating paper is used as a parameter relevant to degradation of the insulating paper. The parameter, however, is not limited to the average degree of polymerization of the insulating paper. For example, the concentration or amount of a substance that is generated due to degradation of the insulating paper may also be used as a parameter relevant to degradation of the insulating paper. The design limit value of the parameter is defined as a value corresponding to the design limit value of the mechanical strength of the insulating paper. The operating time of the oil-filled electrical device that is taken for the parameter to reach the design limit value corresponds to the lifetime of the oil-filled electrical device, namely time Tc shown in FIG. 6. In this case as well, the lifetime assessment and a countermeasure for suppressing degradation of the oil-filled electrical device can be carried out.

The calculation unit is not limited to the one having the configuration as described above. For example, a plurality of blocks may be united into one block. Alternatively, a part of a plurality of functional blocks shown in FIGS. 7 and 13 may be disposed outside the calculation unit.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A lifetime assessment apparatus for an oil-filled electrical device including a winding having a conductor covered with insulating paper, a tank containing said winding, and an insulating oil filling said tank, said lifetime assessment apparatus comprising:
   a measurement unit configured to measure a residual concentration of a causative substance contained in said insulating oil and reacting with said conductor to generate an electrically conductive compound;
   a concentration estimate unit configured to estimate an initial concentration of said causative substance based on an operating time of said oil-filled electrical device and a measurement value of said residual concentration measured by said measurement unit; and
   a comparison unit configured to compare a reference value of said initial concentration with an estimate value of said initial concentration estimated by said concentration estimate unit,
   said reference value being defined as a value for determining whether a main determinant that determines a lifetime of said oil-filled electrical device is generation of said electrically conductive compound or degradation of said insulating paper; and
   an assessment unit configured to assess the lifetime of said oil-filled electrical device, based on a result of comparison between said estimate value and said reference value.

2. The lifetime assessment apparatus for the oil-filled electrical device according to claim 1, said lifetime assessment apparatus further comprising a storage unit configured to store, in advance, a map defining a lifetime of said oil-filled electrical device by a parameter relevant to degradation of said insulating paper, and said initial concentration, wherein said lifetime is defined, based on which of said initial concentration and said reference value is larger, so that said lifetime depends on one of said parameter and said initial concentration, and said assessment unit assesses said lifetime of said oil-filled electrical device based on said result of comparison and said map.

3. The lifetime assessment apparatus for the oil-filled electrical device according to claim 2, wherein when said initial concentration is smaller than said reference value, said lifetime is defined as depending on said parameter, when said initial concentration is larger than said reference value, said lifetime is defined as depending on said initial concentration, and when said result of comparison shows that said estimate value is smaller than said reference value, said assessment unit generates a difference between said lifetime based on said parameter and said operating time and, when said result of comparison shows that said estimate value is larger than said reference value, said assessment unit generates a difference between said lifetime based on said initial concentration and said operating time.

4. The lifetime assessment apparatus for the oil-filled electrical device according to claim 3, wherein a relation between said lifetime and said initial concentration when said initial concentration is larger than said reference value corresponds to a relation between said operating time taken for dielectric breakdown of said winding to occur due to said electrically conductive compound, and said initial concentration.

5. The lifetime assessment apparatus for the oil-filled electrical device according to claim 2, wherein said parameter is an average degree of polymerization of said insulating paper.

6. The lifetime assessment apparatus for the oil-filled electrical device according to claim 5, wherein said lifetime when said initial concentration is smaller than said reference value corresponds to said operating time taken for said average degree of polymerization of said insulating paper to reach a predetermined limit value.

7. The lifetime assessment apparatus for the oil-filled electrical device according to claim 1, wherein said conductor contains copper, and said electrically conductive compound is copper sulfide.

8. The lifetime assessment apparatus for the oil-filled electrical device according to claim 7, wherein said causative substance is a sulfur compound.

9. The lifetime assessment apparatus for the oil-filled electrical device according to claim 8, wherein said sulfur compound is dibenzyl disulfide.

10. A degradation suppression apparatus for an oil-filled electrical device including a winding having a conductor covered with insulating paper, a tank containing said winding, and an insulating oil filling said tank, said degradation suppression apparatus comprising:

a measurement unit configured to measure a residual concentration of a causative substance contained in said insulating oil and reacting with said conductor to generate an electrically conductive compound;

a concentration estimate unit configured to estimate an initial concentration of said causative substance based on an operating time of said oil-filled electrical device and a measurement value of said residual concentration measured by said measurement unit; and a comparison unit configured to compare a reference value of said initial concentration with an estimate value of said initial concentration estimated by said concentration estimate unit, said reference value being defined as a value for determining whether a main determinant that determines a lifetime of said oil-filled electrical device is generation of said electrically conductive compound or degradation of said insulating paper; and an information generation unit configured to generate information concerning a countermeasure for suppressing degradation of said oil-filled electrical device, based on a result of comparison between said estimate value and said reference value.

11. The degradation suppression apparatus for the oil-filled electrical device according to claim 10, wherein said information generation unit generates information for suppressing generation of said electrically conductive compound when said estimate value is larger than said reference value, and generates information for suppressing degradation of said insulating paper when said estimate value is smaller than said reference value.

12. A lifetime assessment method for an oil-filled electrical device including a winding having a conductor covered with insulating paper, a tank containing said winding, and an insulating oil filling said tank, comprising the steps of:

measuring, by a measuring device, a residual concentration of a causative substance contained in said insulating oil and reacting with said conductor to generate an electrically conductive compound;

estimating, by a concentration estimate unit, an initial concentration of said causative substance based on an operating time of said oil-filled electrical device and a measurement value of said residual concentration; and comparing, by a comparison unit, a reference value of said initial concentration with an estimate value of said initial concentration, said reference value being defined as a value for determining whether a main determinant that determines a lifetime of said oil-filled electrical device is generation of said electrically conductive compound or degradation of said insulating paper; and assessing, by an assessment unit, the lifetime of said oil-filled electrical device, based on a result of comparison between said estimate value and said reference value.

13. The lifetime assessment method for the oil-filled electrical device according to claim 12, further comprising the step of preparing a map defining a lifetime of said oil-filled electrical device by a parameter relevant to degradation of said insulating paper, and said initial concentration, wherein said lifetime is defined, based on which of said initial concentration and said reference value is larger, so that said lifetime depends on one of said parameter and said initial concentration, and said step of assessing assesses said lifetime of said oil-filled electrical device based on said result of comparison and said map.

14. The lifetime assessment method for the oil-filled electrical device according to claim 13, wherein when said initial concentration is smaller than said reference value, said lifetime is defined as depending on said parameter, when said initial concentration is larger than said reference value, said lifetime is defined as depending on said initial concentration, and said step of assessing includes the steps of
generating a difference between said lifetime based on said parameter and said operating time, when said result of comparison shows that said estimate value is smaller than said reference value; and
generating a difference between said lifetime based on said initial concentration and said operating time, when said result of comparison shows that said estimate value is larger than said reference value.

15. The lifetime assessment method for the oil-filled electrical device according to claim 14, wherein
a relation between said lifetime and said initial concentration when said initial concentration is larger than said reference value corresponds to a relation between said operating time taken for dielectric breakdown of said winding to occur due to said electrically conductive compound, and said initial concentration.

16. The lifetime assessment method for the oil-filled electrical device according to claim 13, wherein said parameter is an average degree of polymerization of said insulating paper.

17. The lifetime assessment method for the oil-filled electrical device according to claim 16, wherein
said lifetime when said initial concentration is smaller than said reference value corresponds to said operating time taken for said average degree of polymerization of said insulating paper to reach a predetermined limit value.

18. The lifetime assessment method for the oil-filled electrical device according to claim 12, wherein
said conductor contains copper, and
said electrically conductive compound is copper sulfide.

19. The lifetime assessment method for the oil-filled electrical device according to claim 18, wherein
said causative substance is a sulfur compound.

20. The lifetime assessment method for the oil-filled electrical device according to claim 19, wherein
said sulfur compound is dibenzyl disulfide.

21. A degradation suppression method for an oil-filled electrical device including a winding having a conductor covered with insulating paper, a tank containing said winding, and an insulating oil filling said tank, comprising the steps of
measuring, by a measuring device, a residual concentration of a causative substance contained in said insulating oil and reacting with said conductor to generate an electrically conductive compound;
estimating, by a concentration estimate unit, an initial concentration of said causative substance based on an operating time of said oil-filled electrical device and a measurement value of said residual concentration; and
comparing, by a comparison unit, a reference value of said initial concentration with an estimate value of said initial concentration,
said reference value being defined as a value for determining whether a main determinant that determines a lifetime of said oil-filled electrical device is generation of said electrically conductive compound or degradation of said insulating paper; and
generating information, by an information generation unit, concerning a countermeasure for suppressing degradation of said oil-filled electrical device, based on a result of comparison between said estimate value and said reference value.

22. The degradation suppression method for the oil-filled electrical device according to claim 21, wherein
said method of generating information includes the steps of:
generating information for suppressing generation of said electrically conductive compound when said estimate value is larger than said reference value; and
generating information for suppressing degradation of said insulating paper when said estimate value is smaller than said reference value.

* * * * *